US00PP36523P2

(12) United States Plant Patent
Shipley et al.

(10) Patent No.: US PP36,523 P2
(45) Date of Patent: Mar. 4, 2025

(54) ***LEUCOPHYLLUM* SHRUB PLANT NAMED 'Little Lynn'**

(50) Latin Name: ***Leucophyllum frutescens* X *L. langmaniae***
Varietal Denomination: Little Lynn

(71) Applicants: Nicholas Benoit Shipley, Tucson, AZ (US); Russ A. Buhrow, Tucson, AZ (US)

(72) Inventors: Nicholas Benoit Shipley, Tucson, AZ (US); Russ A. Buhrow, Tucson, AZ (US)

( * ) Notice: Subject to any disclaimer, the term of this patent is extended or adjusted under 35 U.S.C. 154(b) by 10 days.

(21) Appl. No.: 18/445,793

(22) Filed: Feb. 5, 2024

(51) Int. Cl.
*A01H 5/02* (2018.01)
*A01H 6/00* (2018.01)

(52) U.S. Cl.
USPC ..... Plt./226

(58) Field of Classification Search
USPC ..... Plt./226
CPC ..... A01H 5/02; A01H 5/00; A01H 6/00
See application file for complete search history.

(56) References Cited

U.S. PATENT DOCUMENTS

PP35,437 P2 * 10/2023 Shipley ..... A01H 6/00 Plt./226

* cited by examiner

*Primary Examiner* — June Hwu

(57) ABSTRACT

A new and distinct *Leucophyllum frutescens* X *L. langmaniae* shrub plant named 'Little Lynn' is characterized by dwarf size (4 feet tall×4 feet wide at maturity), a compact, rounded growth form, possessing large, long lasting, colorfast, fragrant, lilac-colored flowers which are produced abundantly and continuously from April to November at the Sahuarita, Arizona growing location. 'Little Lynn' has among the most winterfast leaves (excellent winter retention of leaves with normal summer color) of any *Leucophyllum* cultivar. 'Little Lynn' has demonstrated excellent growth both in the nursery and in the landscape. 'Little Lynn' is highly resistant to the damping off organisms that normally injure or kill many *Leucophyllum* cultivars. 'Little Lynn' is hardy to USDA zone 7B/8A.

2 Drawing Sheets

Latin name: *Leucophyllum frutescens* X *L. langmaniae.*
Varietal denomination: 'Little Lynn'.

INTRODUCTION

Shrubs of the genus *Leucophyllum* are commonly called Texas Rangers, simply "Rangers" or barometer plant in English and Cenizo in Mexico. The genus consists of about 12 species native to arid portions of Mexico from Puebla in the south northward to the southern portions of Texas. The various "Rangers" have become popular landscape plants throughout the southwestern United States as well as other areas of the world with similar climates and extending into moister areas successfully if the soil has adequate drainage. Seven species of *Leucophyllum* are commonly cultivated, as well as several interspecific hybrid cultivars. The most popularly grown species is *Leucophyllum frutescens*. Many cultivars of this species are grown.

BACKGROUND OF THE INVENTION

The present invention relates to a new and distinct cultivar of *Leucophyllum*. The cultivar originated from an intentional breeding program designed to create new cultivars with improved nursery and landscape performance, as many current *Leucophyllum* cultivars are susceptible to damping off diseases both in the nursery and in the landscape. Many of the existing cultivars also become quite large and require frequent trimming to keep them within the scale of the landscape. Cultivars are also being selected for other horticultural characteristics such as mature plant size and density for reduced maintenance costs as well as improvement of flowering characteristics.

The new cultivar is a selection of the $F_2$ generation resulting from the cross *Leucophyllum frutescens* 'Green Cloud' (unpatented) X *Leucophyllum langmaniae* 'Lynn's Legacy' (unpatented) utilizing *Leucophyllum frutescens* 'Green Cloud' as the female parent and *Leucophyllum langmaniae* 'Lynn's Legacy' as the male parent. The new selection exhibits a dwarf, compact, rounded form, having winterfast (reduced winter leaf drop and retention of normal summer leaf color) evergreen leaves, possessing excellent nursery and landscape adaptation and producing large, fragrant, long lasting, everblooming lilac-colored flowers, as well as possessing excellent resistance to damping off diseases and is the object of this application.

SUMMARY OF THE INVENTION

Among the features that distinguish the new *Leucophyllum langmaniae* cultivar from all other available and commercial varieties of *Leucophyllum langmaniae* known to the inventor are the following combination of characteristics: dwarf, compact, rounded growth form, winterfast leaves, everblooming, long lasting, large, fragrant, lilac colored flowers on plants with excellent tolerance (improved growth and survival under conditions of variable water availability and waterlogging as well as tolerance to compacted soil in the landscape compared to most existing cultivars) to nursery and landscape culture as well as excellent resistance to damping off diseases present at the production facility. The specific damping off organisms have not been identified.

*Phymatotrucopsis omnivora* is noted as a problem in some landscape plantings in the literature but that is a soil fungus and unlikely in potting soil in containers so clearly other pathogens are a factor for many cultivars. A search of the literature failed to locate reports of other specific fungi commonly causing the problem in *Leucophyllum*.

Plants were asexually reproduced at a commercial nursery near Sahuarita, Arizona.

The asexual propagation procedure is as follows: Semi-hardwood cuttings 4-5" long are prepared by removing the lower leaves, then dipping the cleared portion of the cut into a 1:10 solution of DIP'N GROW™. The cuttings are then inserted about one inch into prepared peat trays. The trays are moved to a mist house with mist applied every 20 minutes and temperature maintained between 70-85° F. Rooting is generally complete within 4 weeks.

The foregoing characteristics and distinctions come true to form and are established and transmitted through succeeding propagations. The present invention has not been evaluated under all possible environmental conditions, such that the phenotype may vary with variations in environment without a change in the genotype of the plant.

BRIEF DESCRIPTION OF THE DRAWINGS

The accompanying photographs illustrate *Leucophyllum* 'Little Lynn' growing near Sahuarita, Arizona, depicted in color as nearly correct as it is possible to make in a color illustration of the character.

DETAILED PLANT DESCRIPTION

Figure 1:
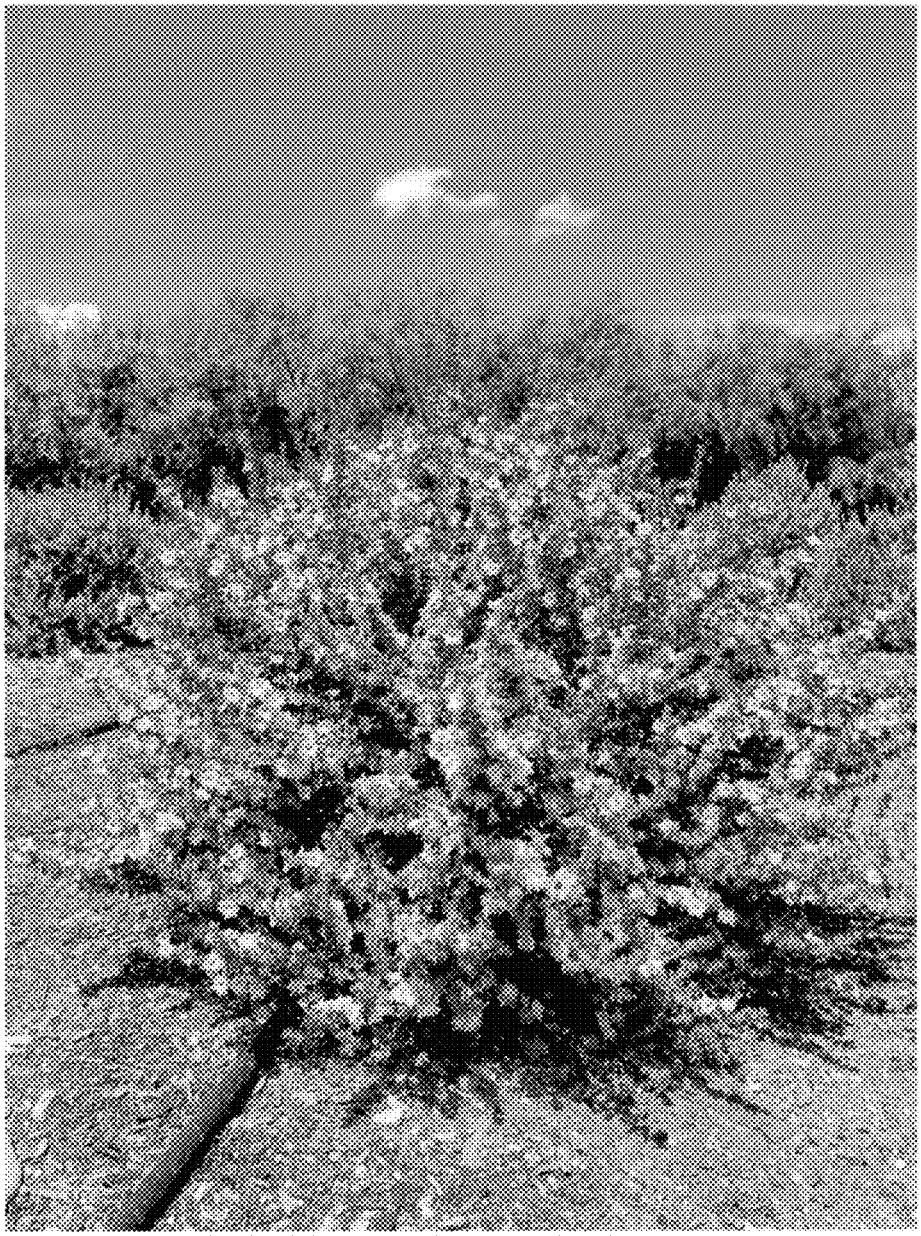
FIG. 1 shows *Leucophyllum* 'Little Lynn' aged 5 years growing under irrigation at a commercial nursery near Sahuarita, AZ.
Figure 2:
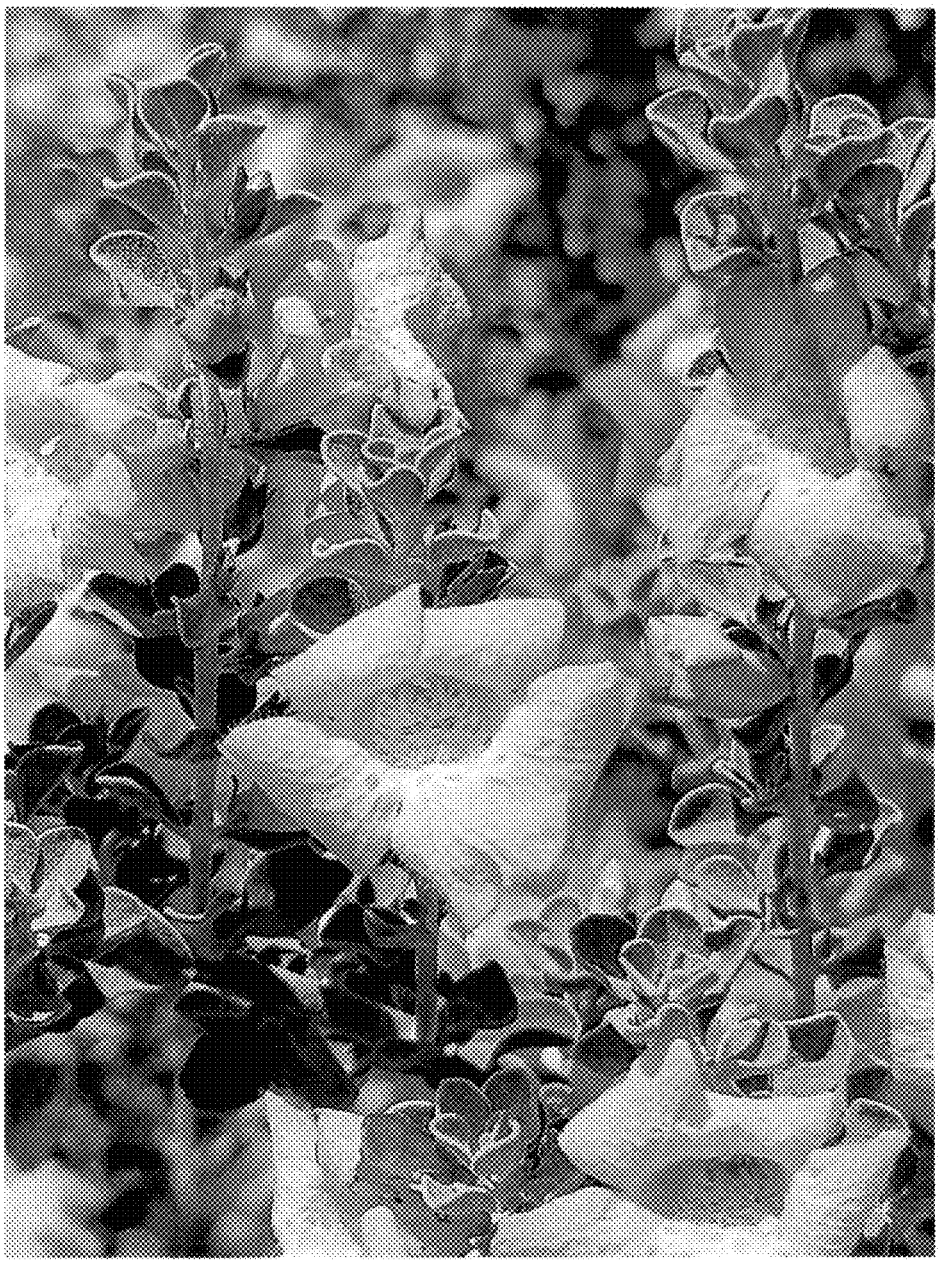
FIG. 2 shows buds, leaves and flowers of *Leucophyllum* 'Little Lynn'.

The following is a detailed description of the new *Leucophyllum* 'Little Lynn' plant based upon the original selection aged 5 years growing in the ground near Sahuarita, Arizona. The floral and leaf characters were described from a *Leucophyllum* 'Little Lynn' plant growing in a #5 nursery pot in Tucson, AZ.

The color descriptions are based upon the 5$^{th}$ edition R.H.S. Colour Chart, copyright 2007. Color names other than common usage are as listed in *COLOR Universal Language and Dictionary of Names*, by Kenneth L. Kelly and Deane B. Judd; National Bureau of Standards special publication 440. Washington, D.C.: U.S. Department of Commerce, National Bureau of Standards, December 1976.

'Little Lynn' is a rounded, medium sized, evergreen woody shrub reaching about 4 feet tall×4 feet wide at maturity which is a dwarf plant compared to typical *Leucophyllum* cultivars. At age 5 years the original plant measures 3.5 feet tall×3.5 feet wide in the ground under irrigation.

Typically, *Leucophyllum* cultivars exhibit considerable leaf drop during winter. 'Little Lynn' has winter fast leaves, presenting a more attractive winter form. No insect or disease problems have been noted with this plant. 'Little Lynn' is hardy to at least 10° F., USDA zone 7B/8A. 'Little Lynn' blooms from April to November at the Sahuarita location and has everblooming tendencies stronger than most *Leucophyllum* cultivars. The flowers are single and are produced from the leaf axils, heaviest near the stem apex but also occurring on small lateral branches and throughout the canopy. The flowers are mildly and pleasantly fragrant. Individual flowers are unusually long lasting and colorfast for the genus, the individual flowers remaining in attractive condition for up to 5 days. The spent flowers are shed soon after closing. A check of flowering plants in #5 nursery containers in early September 2024 at the Sahuarita grow yard gave an average of 2.6 flowers per stem. It should be noted that flower numbers and density are highly variable with growth conditions and season and are probably not a particularly diagnostic character.

Young, matured stems are terete, densely puberulent with stellate hairs. Stem color is 138C, hair color 157A. Young stems measure 1.3-1.6 mm in diameter and internodes vary in length from 1-12 mm. Branch angles vary from 45-80°. Young stems are flexible, becoming strong and stiff with increasing diameter. Stems of intermediate age measure 1.6-3.5 mm in diameter, the hairs becoming caducous with age. The stem at this stage of development is colored 199A. Larger stems 3.5-6.0 mm in diameter have become glabrous and covered with an elongated reticulum colored 199D. The areas intervening between the reticulum are colored 199A.

Stipules are absent. Axillary buds measure 0.4 mm×0.4 mm and are more or less rounded in shape, canescent with stellate hairs, color NN155C, hairs colored NN155D. Leaves are alternate, simple, sessile, spatulate to broadly oblanceolate, the margin entire except weakly acuminate at the apex. The leaf base is narrowly acute. Leaves measure 5-21 mm long×4-9 mm wide.

Leaf adaxial surface colored 137B is puberulent with stellate hairs, less densely than abaxial side, the hairs colored 157C. The midrib is depressed into the leaf ¾ of the length of the leaf from the base. The midrib is colored 138C, canescent with stellate hairs colored 157C. Secondary veins are obscure.

The abaxial leaf surface (colored N138B) is puberulent with stellate hairs, which are both more concentrated and larger along the raised midrib, which is visible for ⅘ of the leaf length. The midrib is colored 138B, the hairs colored 157C.

Flower pedicels are terete and measure 2-3 mm in length× 0.75 mm in diameter, color 144A. The surface is moderately covered with stellate hairs colored NN155D.

The calyx is 5 lobed, flaring, basally united, color 144A, measuring 4 mm in length. Calyx diameter at the base is 2 mm, 4-6 mm at the apex. The lobes are 3.25 mm long, basally 0.75 mm wide, lanceolate in shape, basally truncate, apically acute, margins entire. Abaxial surface of calyx pubescent with scattered stellate hairs, these densest at the base, colored NN155D. Lobe margins sparsely ciliate, the hairs colored NN155D. Adaxial surface of calyx (color 144A) with sparse, very short, straight hairs colored NN155D.

Mature buds are oblanceoloid in shape and glabrous, measuring 18 mm long×6 mm in diameter at the widest part. The upper 2 petal lobes enclose the lower 3 in bud. The apex of the bud is colored 76A. The adaxial side of the tube has a base color midway between 76A and 76B. Faint longitudinal lines aligned with the petal lobe centers measure 0.5 mm wide colored 76A. The abaxial side of the tube has a base color of 76D with scattered spots 0.5 mm in diameter colored 76B.

Flowers are trumpet shaped with 5 petal lobes. The flowers measure 25-29 mm long, 21-32 mm across the lateral face of the flower and 20-25 mm across the vertical face. The tube opening measures 5-8 mm vertically×6-11 mm horizontally. The floral tube interior lower portion is spotted with color 76A, spot diameter about 0.5 mm on a base color of NN155A. The lower interior tube is villous, hairs colored NN155A. The interior tube upper portion is pubescent with both the surface and hairs colored 76B. Petal lobes are orbicular, the upper 2 erect, the lower 3 erect to extended. Axially the petal lobe margins are entire, slightly crisped, ciliate (more strongly so on the lower petal lobes), hairs and petal lobes both colored 76B. The surface of the upper 2 lobes is glabrous. The upper half of the lateral lobes is glabrous. The lowest petal lobe is villous as are the lower halves of the lateral petal lobes (hairs colored 76B). Externally the petal lobes are glabrous, color 76B.

Staminode is absent. Stamens 4, of 2 lengths, epipetalous, attached near the base, explanate. Short stamens measure 6.5 mm long, filaments 0.25 mm in diameter, sigmoid. Long stamens measure 8 mm long, filaments 0.33 mm diameter. Filaments grade in color from NN155D at the base to 76D just below the anther. Anthers measure 1.5 mm long×0.5 mm wide, color 162B.

Pollen nearly spherical, measuring 30 μ in diameter, color 155B.

Pistil single, ovary superior with 2 carpels, measuring 12 mm in length and 1.5 mm in diameter at the ovary. The ovary is conical, widest at the base, 2 mm long and 1.5 mm in diameter, glabrous, color 144B. Style terete, glabrous, 9 mm in length, 0.4 mm in diameter, flaring just below the stigma, color NN155D. Stigma fan shaped, glabrous, 1.0 mm long× 1.0 mm wide×0.4 mm thick, color N155A.

Fruits are not produced either under Sahuarita or Tucson conditions. The ovaries shed soon after the flowers. No fruit or seed have been observed to date.

COMPARISONS TO RELATED *LEUCOPHYLLUMS*

Compared to its female parent, *Leucophyllum frutescens* 'Green Cloud' (unpatented), 'Little Lynn' is about ⅖ the size of 'Green Cloud'. The flowers of 'Green Cloud' are colored 64D compared to 76B for those of 'Little Lynn'.

Compared to its male parent, *Leucophyllum langmaniae* 'Lynn's Legacy' (unpatented), 'Little Lynn' is about half as large and rounded, compared to broader than tall for 'Lynn's Legacy'. 'Lynn's Legacy' reaches 6+ feet tall by 10 feet wide under Sahuarita conditions, while 'Little Lynn' reaches about 4×4 feet. The flower color of the two cultivars is similar, 76A for 'Lynn's Legacy' and 76B for 'Little Lynn'. The flowers of 'Little Lynn' are considerably larger than 'Lynn's Legacy', measuring 19-20 mm across the face for 'Lynn's Legacy' and 21-32 mm for 'Little Lynn'. 'Little Lynn' has improved damping off resistance compared to 'Lynn's Legacy'.

Compared to *Leucophyllum frutescens* 'San Antonio Rose', (U.S. Plant Pat. No. 33,454-P2), 'Little Lynn' is a smaller plant (4 feet×4 feet compared to 5×5 feet for 'San Antonio Rose'. Flowers of 'San Antonio Rose' measure across the lateral flower face 19-24 mm, color 75A while those of 'Little Lynn' measure 21-32 mm wide, color 76B. Floral fragrance of 'Little Lynn' is fainter than that of 'San Antonio Rose'.

Compared to *Leucophyllum frutescens* 'Convent' (unpatented), 'Little Lynn' is a smaller plant with a rounded shape while 'Convent' is more upright in growth habit. 'Convent' flowers are colored N74B while those of 'Little Lynn' are colored 76B. 'Convent' is highly susceptible to damping off while damping off has not been observed in the nursery or in the ground with 'Little Lynn'.

Compared to *Leucophyllum frutescens* 'Compacta' (not patented), 'Little Lynn' is a much smaller plant with flowers colored 76B while those of 'Compacta' are colored 75A.

Compared to 'Heavenly Cloud' (not patented), an interspecies hybrid between *Leucophyllum frutescens* and *L. laevigatum*, 'Little Lynn' is about half as large. Flowers of 'Little Lynn' are colored 76B compared to 94C for 'Heavenly Cloud'.

Compared to *Leucophyllum frutescens* 'White Cloud' (not patented), 'Little Lynn' is ⅓ as large. 'White Cloud' has white flowers compared to those of 'Little Lynn', colored 76B. Damping off resistance is stronger in 'Little Lynn'.

Compared to *Leucophyllum* hybrid 'MSWNRascon' (U.S. Plant Pat. No. 33,806-P2), 'Little Lynn' has a rounded form compared to an upright, spreading form for 'MSWNRascon'. The flowers of 'MSWNRascon' are colored 77A, 77B while those of 'Little Lynn' are colored 76B. The mature size of 'MSWNRascon' is roughly double that of 'Little Lynn'. Flowers of 'Little Lynn' are fragrant while those of 'MSWNRascon' are not. Flowers of 'Little Lynn' last up to 5 days while those of 'MSWNRascon' last 2-3 days.

Compared to *Leucophyllum frutescens* 'GREHJS' (U.S. Plant Pat. No. 33,638-P2), 'Little Lynn' has 5 flower petal lobes colored 76B, while 'GREHJS' has 6 petal lobes of differing colors, the upper ones colored 75A. The growth habit of 'GREHJS' is upright and spreading, while 'Little Lynn' is rounded.

Compared to 'MSWNHelei' (U.S. Plant Pat. No. 34,884-P2), a low growing shrub with a mounding habit, 'Little Lynn' is rounded in shape. The flowers of 'MSWNHelei' are colored N82B compared to those of 'Little Lynn' colored 76B.

Compared to 'Purple Rain' (US-20230200272-P1), 'Little Lynn' is about half as large, with flowers colored 76B compared to 80D for 'Purple Rain'.

Compared to *Leucophyllum langmaniae* 'Rio Bravo' (unpatented), 'Little Lynn' is a smaller plant (4×4 feet compared to 7×7 feet). The flowers of 'Rio Bravo' are colored 91A while those of 'Little Lynn' are colored 76B.

Compared to 'Microburst' (U.S. Plant Pat. No. 35,437 P2), 'Little Lynn' is slightly larger. The flowers of 'Microburst' are colored N88B and those of 'Little Lynn' are colored 76B. The fragrance of 'Microburst' flowers is considerably stronger than those of 'Little Lynn'. Both cultivars have excellent resistance to damping off diseases. 'Little Lynn' has not been tested under the extreme conditions of standing water that 'Microburst' survived unscathed, but both cultivars experience zero loss under the nursery and landscape conditions so far encountered.

We claim:

1. A new and distinct *Leucophyllum* shrub plant substantially as described and illustrated herein.

* * * * *